US006419291B1

(12) United States Patent
Preta

(10) Patent No.: US 6,419,291 B1
(45) Date of Patent: Jul. 16, 2002

(54) ADJUSTABLE FLEXIBLE VACUUM GRIPPER AND METHOD OF GRIPPING

(76) Inventor: John Preta, 1900 S. Eads St. Apt. 136, Arlington, VA (US) 22202

( * ) Notice: Subject to any disclaimer, the term of this patent is extended or adjusted under 35 U.S.C. 154(b) by 0 days.

(21) Appl. No.: 09/792,047

(22) Filed: Feb. 26, 2001

(51) Int. Cl.$^7$ .............................. B25J 15/06; B66C 1/46
(52) U.S. Cl. .................. 294/64.1; 294/119.3; 294/902; 901/40; 901/47
(58) Field of Search .............................. 294/64.1, 64.2, 294/64.3, 65, 119.3, 86.4, 902, 907; 901/30, 31, 39, 40, 45, 47

(56) References Cited

U.S. PATENT DOCUMENTS

| | | | |
|---|---|---|---|
| 3,219,792 A | * 11/1965 | Pederson | 219/121.12 |
| 3,387,718 A | * 6/1968 | Roth et al. | 294/119.3 |
| 3,601,248 A | * 8/1971 | Gerard | 198/866 |
| 3,696,596 A | * 10/1972 | Wegscheid | 294/64.1 |
| 3,716,264 A | 2/1973 | Pearne et al. | |
| 3,913,307 A | * 10/1975 | Cardinal, Jr. | 294/119.3 |
| 4,045,073 A | * 8/1977 | Mosterd | 294/119.3 |
| 4,561,687 A | 12/1985 | Bostrom | |
| 4,600,229 A | * 7/1986 | Oten | 294/64.1 |
| 4,997,435 A | 3/1991 | Demeter | |
| 5,217,468 A | 6/1993 | Clement | |
| 5,403,056 A | 4/1995 | Wallace | |
| 5,493,995 A | 2/1996 | Chowdhury | |
| 5,536,056 A | 7/1996 | Clarke et al. | |
| 5,947,995 A | 9/1999 | Samuels | |
| 5,964,568 A | 10/1999 | Codatto | |
| 6,102,459 A | 8/2000 | Pabst et al. | |
| 6,159,230 A | 12/2000 | Samuels | |

FOREIGN PATENT DOCUMENTS

| | | |
|---|---|---|
| SU | 197 705 | 5/1977 |
| SU | 1060-471 | 12/1983 |
| WO | 88/03462 | 5/1988 |

* cited by examiner

Primary Examiner—Dean J. Kramer
(74) Attorney, Agent, or Firm—John Preta

(57) ABSTRACT

A flexible vacuum gripper device and method of gripping. The device includes a housing, an inflatable gripper element defining an internal chamber and being radially or circumferentially expandable, the inflatable gripper element having a front end which is adapted to grip an object and a rear end coupled to the housing, a vacuum source communicating with the internal chamber of the inflatable gripper element, and a pressure source communicating with the inflatable gripper, wherein the vacuum gripper device is adapted to grip the object using vacuum formed in the internal chamber and wherein the inflatable gripper element is adapted to be inflated using the pressure source. The method includes adjusting a position of the flexible gripper element with respect to the housing by moving the flexible gripper element towards or away from the housing, positioning the inflatable gripper against the object, inflating the inflatable gripper using the pressure source, and forming a vacuum in the internal chamber using the vacuum source, wherein the vacuum gripper device is adapted to vacuum grip the object while the inflatable gripper element is inflated.

20 Claims, 10 Drawing Sheets

ADJUSTABLE FLEXIBLE VACUUM GRIPPER AND METHOD OF GRIPPING

BACKGROUND OF THE INVENTION

1. Field of the Invention

The invention relates to a flexible vacuum gripper which is adapted to gripping objects of varying shapes such as those which have irregular shapes and/or non-symmetrical shapes. The gripper utilizes a gripping element which is circumferentially and/or radially adjustable so as to be able to conform to irregular-shaped objects of varying size. The flexible gripper may have particular advantage in gripping objects which are lodged and/or trapped inside conduits and/or tunnels and/or underground bore holes or the like. The flexible gripper may also be used to remove objects trapped or lodged within various body conduits, e.g., objects which are trapped inside an animals throat. It may even have beneficial use in facilitating birthing, e.g., by gripping the head of life being for extraction.

2. Discussion of Background Information

Grippers which utilize vacuum to grip objects are known. However, such grippers generally cannot reliably grip irregularly shaped objects because they require that a seal be maintained between a surface of the object and a contacting surface on the gripper itself.

Thus, for example, U.S. Pat. No. 4,561,687 provides a gripper having a workpiece contact surface which ensures an air tight seal between the gripper and the workpiece. However, such a contact surface cannot be said to be adjustable to objects of varying size. Moreover, it is clear that such a gripper design cannot function effectively to grip objects of irregular-shape and/or non-symmetrical objects.

U.S. Pat. No. 5,964,568, the disclosure of which is expressly incorporated by reference in its entirety, provides for a transfer unit with a block containing wells in which suckers are located. The wells comprise a border made of a sealing and friction material. The peripheral wall of the sucker is flexible enough to permit axial movement of the lip between an expanded position in which the lip projects above the border of the well and a contracted position in which the lip is coplanar with this border. The internal space of the sucker and the internal space of the well around the sucker are both connected to a vacuum source by respective narrow channels whose cross sections are approximately the same as each other. The size of the cross sections of the narrow channels is such that there is negligible loss of vacuum inside the sucker when a work piece is placed against the lip but not against the border of the well. However, such a sucker cannot be said to be adjustable to objects of varying size. Moreover, such a gripper design cannot function effectively to grip objects of irregular-shape and/or non-symmetrical objects.

U.S. Pat. No. 6,102,459, the disclosure of which is expressly incorporated by reference in its entirety, provides for an assembly for releasably securing objects by the use of a vacuum comprising a body having a fluid inlet port, a fluid outlet port, a fluid flow channel extending between the fluid inlet port and the fluid outlet port, a vacuum port, a low pressure channel extending between the vacuum port and the fluid flow channel, a sensing member receiving channel and a sensing member having a fluid flow regulation portion and a sensing portion, said sensing portion is further adapted to be movably received by the sensing member receiving channel, the sensing member being movable from a closed position to an open position, whereby when the sensing member is in the closed position the fluid flow channel is closed to the flow of fluids, and when the sensing member is in the open position the fluid flow channel is open to the flow of fluids, and when fluids flow through the flow channel a low pressure condition is created within the low-pressure channel. However, such a sucker cannot be said to be adjustable to objects of varying size. Moreover, such a gripper design cannot function effectively to grip objects of irregular-shape and/or non-symmetrical objects.

U.S. Pat. No. 5,403,056, the disclosure of which is expressly incorporated by reference in its entirety, provides for a robotic hand on a robot that is capable of picking-up several generally flattened articles in a stack form in a gentle non-damaging manner. The robotic hand has a manifold for directing controlled pressure air and a set of gripper finger assemblies extending therefrom. Each finger assembly has a rigid finger support member and an inflatable bladder extending along its length. The bladders are in communication with the chamber of the manifold and an external source of positive and negative pressure air. The robotic hand is capable of positioning itself over an article to be picked-up with the set of gripper finger assemblies encompassing the article. Pressurized air is directed through the manifold and into the bladders of the finger assemblies. The bladders expand sufficiently to grasp sides of the article. The robotic hand is moved to a position over another article wherein the bladders of the finger assemblies are deflated by drawing a vacuum through the manifold to cause the first article to drop onto the second article. Reinflating the bladders causes the gripper finger assemblies to grasp the two articles. However, such a hand cannot be said to be adjustable to objects of varying size. Additionally, the hand gripper uses positive and negative pressure to inflate and deflate bladders for securing the sides of flat objects, and does not use vacuum to grip the objects themselves. Moreover, such a gripper design cannot function effectively to grip objects of irregular-shape and/or non-symmetrical objects.

U.S. Pat. No. 3,716,264, the disclosure of which is expressly incorporated by reference in its entirety, provides for an inflatable gripper that is capable of picking-up bricks. The device appears to utilize bladders which expand sufficiently to grasp sides of the brick. However, such a design cannot be said to be adjustable to objects of varying size. Moreover, such a gripper design cannot function effectively to grip objects of irregular-shape and/or non-symmetrical objects.

U.S. Pat. No. 5,943,995, the disclosure of which is expressly incorporated by reference in its entirety, provides for an elongated, flexible teat cup liner of an improved design which can accommodate teats of varying lengths without fear of teat damage or inefficient machine milking. The liners include an apertured mouthpiece adjacent one end thereof, with an elongated, intermediate barrel presenting an inwardly collapsible teat-receiving region and a lowermost connecting tube adapted for connection to a constant vacuum source, such as, e.g., a milk claw. The liners have a barrel wall of gradually and progressively decreasing wall thickness for creating a differential resistance to inward collapse of the teat-receiving region of the barrel. The decrease in barrel wall thickness assures a relatively high resistance to inward collapse at a first location adjacent the mouthpiece, and a gradual and progressive decrease in such resistance to inward collapse along an axial length of the teat receiving region of the barrel. The connecting tube includes a segment intermediate the remote end of the liner and the barrel which is of reduced wall thickness to promote bending of the connecting tube under the combined weight of the liner and the attached shell to thereby inhibit vacuum-drawn airflow through the central channel when the mouthpiece is unattached to an animal's teat. However, such a milker tea cup cannot be said to be an object gripper, much less, a gripper which is adjustable to objects of varying size. Moreover, such a design is specifically limited to accommodating teats and cannot function effectively to grip objects of irregular-shape and/or non-symmetrical objects.

U.S. Pat. No. 5,536,056, the disclosure of which is expressly incorporated by reference in its entirety, provides for an improved gripping and pinching device particularly useful with laboratory glassware and adaptable for use with a robot or automated system. The device uses flexible tubing as a gripper, eyedropper pincher and as a pinch valve which biases and releases test tubes, vials or the like upon removal and application of a vacuum or pressurizing means. However, such a gripper cannot be said to be a gripper which is adjustable to objects of varying size. Additionally, the gripper uses positive and negative pressure to inflate and deflate a tube for securing the sides of objects rather than using vacuum to grip the objects themselves. Moreover, such a gripper design cannot function effectively to grip objects of irregular-shape and/or non-symmetrical objects.

U.S. Pat. No. 4,997,435, the disclosure of which is expressly incorporated by reference in its entirety, provides for a percutaneous catheter with encapsulating receptacle comprises a first catheter having a proximal and distal end, several struts attached to the distal end of the first catheter and extending distally therefrom in a cup-shaped form, a second, inner catheter received within the first, and a pocket-shaped sheath received between the several struts and opening in the distal direction, the sheath having a proximal portion secured to the distal end of the second, inner catheter, and a distal portion secured to the distal ends of the several struts, whereby rotation of the first catheter, relative the second catheter, twists and closes the distal end of the sheath. A third, outer catheter is also disclosed within which the first and second catheters, and associated struts and sheath, are receivable. Also disclosed is a method for positioning the catheter adjacent an object, or receiving the object within the sheath and enclosing the sheath about the object to facilitate treatment of the object. However, the pocket-shaped sheath does not itself grip objects and cannot be said to be a gripper which is adjustable to objects of varying size. Additionally, the device does not use positive pressure to inflate a gripper element which is capable of gripping objects. Instead, an object grasping device is used to grip objects within the sheath. Moreover, such a gripper design cannot function effectively to grip objects of irregular-shape and/or non-symmetrical objects.

U.S. Pat. No. 5,217,468, the disclosure of which is expressly incorporated by reference in its entirety, provides for a tissue retrieval apparatus for laparoscopic procedures that includes a longitudinally extending tube having a tip end insertible into a patient. The tip end is formed to be radially expandable in response to withdrawal of tissue into the tip end of the tube. Tissue can be withdrawn into the tip end of the tube by using graspers or other devices that can be extended to engage and hold tissue. To reduce the possibility of contamination of healthy tissue, an elastic sheath is attached to cover the tip end of the tube. The elastic sheath is formed to radially expand in response to radial expansion of the tip end of the tube during withdrawal of tissue into the tip end of the tube. However, the elastic sheath does not itself grip objects and cannot be said to be a gripper which is adjustable to objects of varying size. Additionally, the device does not use positive pressure to inflate a gripper element for gripping objects. Instead, a device is used to grip objects within the elastic sheath. Moreover, such a gripper design cannot function effectively to grip objects of irregular-shape and/or non-symmetrical objects.

U.S. Pat. No. 5,947,995, the disclosure of which is expressly incorporated by reference in its entirety, provides for a catheter that has a central lumen so that it may be positioned by a guidewire within a tubular structure of the human body. The catheter has attached to its distal end an inflatable cuff featuring an inflation space with a ring-like cross section. A pouch is circumferentially attached to the cuff. The catheter features an inflation lumen that is in communication with the inflatable cuff. The proximal port of the inflation lumen receives a syringe so that the cuff may be inflated when the cuff and pouch are positioned within a tubular structure. A filament passes through the inflation space of the cuff and the inflation lumen and exits the proximal port of the inflation lumen. As a result, the cuff may be cinched so that the pouch is closed in a purse-string fashion to capture an object in the tubular structure. The object may then be removed from the patient's body. However, the inflatable cuff does not itself grip objects and cannot be said to be a gripper which is adjustable to objects of varying size. Additionally, the device does not use positive pressure to inflate a gripper element, while the gripper element itself grips objects using a vacuum. Instead, an object grasping device is used to gather objects within a pouch. Moreover, such a device cannot function effectively to grip objects of irregular-shape and/or non-symmetrical objects.

U.S. Pat. No. 6,159,230, the disclosure of which is expressly incorporated by reference in its entirety, provides for a device for removing undesirable material from a tubular structure within the human body features a cylindrical body with a lumen therethrough. The distal portion of the body is divided into a number of flexible members. An inflatable cuff is attached to the flexible members. When the cuff is inflated, the members flex radially outwardly so that the distal opening of the lumen is expanded. An inflation tube is used to inflate and deflate the cuff by means of a syringe. An elastomeric membrane sleeve surrounds the flexible members so that the latter are contracted towards their original position when the cuff is deflated. The sleeve also prevents material from escaping between the flexible members when the cuff is inflated. However, the inflatable cuff does not itself grip objects and cannot be said to be a gripper which is adjustable to objects of varying size. Additionally, the device does not use positive pressure to inflate a gripper element while the gripper element itself grips objects using a vacuum. Instead, a balloon is used to gather objects within an expanding cuff. Moreover, such a device cannot function effectively to grip objects of irregular-shape and/or non-symmetrical objects.

SU 1060-471-A provides a device for gripping which appears to utilize an inflatable bag and vacuum gripping. However, such a design does not provide for adjustably moving a gripper element with respect to a housing. Moreover, this design lacks a gripper element having folds arranged substantially axially.

SU 556-940 provides a device for gripping which appears to utilize an inflatable granule-filled bag having in which the bag is subjected to vacuum in order for it to assume an objects shape. However, such a design does not apply vacuum to the object to be gripped. Additionally, this design does not provide for adjustably moving a gripper element with respect to a housing. Moreover, this design lacks a gripper element having folds arranged substantially axially.

WO 88/03462 provides a device for gripping which appears to utilize an inflatable bellows and vacuum for gripping. However, such a design does not provide for adjustably moving a gripper element with respect to a housing. Moreover, this design lacks a gripper element having folds arranged substantially axially.

SUMMARY OF THE INVENTION

The invention therefore provides for a flexible gripper which includes an pressure expandable gripper element adapted to sealing contact an object. In this way, the gripper element uses vacuum to grip the objects. The invention has particular advantage in gripping objects which are of irregular shape and/or of non-symmetrical shape, since the gripper element is capable of sealingly conforming to an irregular surface of the object so as to effectively grip the object using low pressure or vacuum.

According to one embodiment of the invention, there is provided a flexible vacuum gripper device comprising a housing, an inflatable gripper element defining an internal chamber and being radially expandable, the inflatable gripper element having a front end which is adapted to grip an object and a rear end coupled to the housing, a vacuum source is provided for communicating with the internal chamber of the inflatable gripper element, a pressure source is also provided for communicating with the inflatable gripper. The vacuum gripper device is adapted to grip the object using vacuum formed in the internal chamber and the inflatable gripper element is adapted to be inflated using the pressure source.

According to another embodiment, there is provided a flexible vacuum gripper device comprising a housing, an inflatable gripper element defining an internal chamber and comprising a rear portion coupled to the housing and a front portion which can be one of radially and circumferentially expandable, the front end being conformable to the shape of an object, a vacuum source communicating with the internal chamber of the inflatable gripper element, a pressure source communicating with the inflatable gripper, and one of a movable gripper support being fixed to the rear end portion of the gripper element for allowing the gripper element to move axially with respect to the housing, or the front end portion of the gripper element comprising a plurality of folds which are arranged substantially parallel to an axis thought the housing, wherein the vacuum gripper device is adapted to grip the object using vacuum formed in the internal chamber and wherein the inflatable gripper element is adapted to be inflated using the pressure source.

The rear end of the inflatable gripper element may be non-expandably coupled to the movable gripper support. The housing may comprise a front end portion which engagingly supports an outside surface of the inflatable gripper element. The device may further comprise a movable support which engagingly supports an outside surface of the inflatable gripper element. The inflatable gripper element may comprise an inner wall, an outer wall, and at least one inflatable chamber disposed between the inner and outer walls which capable of being inflated. The device may further comprising a viewing device adapted to view the internal chamber of the inflatable gripper element.

The movable gripper support may be coupled to movable extender rod disposed within the housing. The movable extender rod may comprise a tube which adapted to receive a viewing device and the device may further comprise a lens cap disposed at a front end of the extender rod. The device may further comprise a movable support having a front end which adjustably supports an outside surface of the inflatable gripper element, and the inflatable gripper element may comprise an inner wall, an outer wall, and at least one inflatable chamber disposed between the inner and outer walls which capable of being inflated. The plurality of folds may allow the inflatable gripper element to expand radially, and the device may further comprise a plurality of gripper supports attached to the inflatable gripper element.

The device may further comprise at least one vacuum conduit disposed within the housing and at least one pressure conduit disposed within the housing, wherein the vacuum conduit connects the vacuum source to the internal chamber and wherein the pressure conduit connects the pressure source to the inflatable gripper element. The device may further comprise a movable support having a front end which adjustably supports an outside surface of the inflatable gripper element, the inflatable gripper element comprising an inner wall, an outer wall, and at least one inflatable chamber disposed between the inner and outer walls which capable of being inflated, and the inflatable gripper element comprising a plurality of gripper supports attached to the inflatable gripper element. At least the front end portion of inflatable gripper element may comprise a textured surface which is adapted to ensure a significant amount vacuum gripping between the inflatable gripper element and the object. At least one of the pressure source and the vacuum source may be attached to the housing.

The inflatable gripper element may comprise one of a circular cross-sectional shape and a polygonal cross-sectional shape. The device may further comprise a robot arm coupled to the housing. The housing may be one of axially flexible and axially bendable. The device may further comprise a mechanism for additionally retaining the object, the mechanism comprising at least two substantially oppositely arranged arms which are movable towards and away from the object.

The invention also provides for a flexible vacuum gripper device comprising a housing having a front end, a gripper element defining an internal chamber and being radially or circumferentially expandable, the gripper element comprising an inner wall, an outer wall, a plurality of stitches connecting the inner wall and the outer wall, and at least one inflatable chamber disposed between the inner and outer walls which capable of being inflated, the inflatable gripper element having an expandable and conformable front end which is adapted to grip an object and a rear end coupled to the front end of the housing, a vacuum source communicating with the internal chamber of the inflatable gripper element, a pressure source communicating with the inflatable gripper element, and one of a movable gripper support being fixed to the rear end of the gripper element for allowing the gripper element to move axially with respect to the housing, or the front end of the gripper element comprising a plurality of folds which are arranged substantially parallel to an axis thought the housing, wherein the inflatable gripper element is adapted to be inflated using the pressure source.

A method of gripping an object is also provided which uses a flexible vacuum gripper device which includes a housing, an inflatable gripper element defining an internal chamber and being radially expandable, the inflatable gripper element having a front end adapted to grip an object and a rear end coupled to the housing, a vacuum source communicating with the internal chamber of the inflatable gripper element, and a pressure source communicating with the inflatable gripper, the method comprising adjusting a position of the flexible gripper element with respect to the housing by moving the flexible gripper element towards or away from the housing, positioning the inflatable gripper element against the object, inflating the inflatable gripper using the pressure source, and forming a vacuum in the internal chamber using the vacuum source, wherein the vacuum gripper device is adapted to vacuum grip the object while the inflatable gripper element is inflated.

The rear end of the inflatable gripper element may be non-expandably coupled to a movable gripper support. The housing may comprise a frond end which supports an outside surface of the inflatable gripper element. The device may further comprise a movable support having which supports an outside surface of the inflatable gripper element. The inflatable gripper element may comprise an inner wall, an outer wall, and at least one inflatable chamber disposed between the inner and outer walls which capable of being inflated. The device may further comprise a viewing device adapted to view the internal chamber of the inflatable gripper element. The rear end of the inflatable gripper element may be coupled to a movable gripper support, wherein the movable gripper support is coupled to movable extender rod disposed within the housing. The movable extender rod may comprise a tube which adapted to receive a viewing device and wherein the device further comprises a lens cap disposed at a front end of the extender rod.

The device may further comprise a movable support having a front end which adjustably supports an outside surface of the inflatable gripper element, wherein the inflatable gripper element comprises an inner wall, an outer wall, and at least one inflatable chamber disposed between the inner and outer walls which capable of being inflated. The inflatable gripper element may comprise at least one of a plurality of folds which allow the inflatable gripper element to expand radially, and a plurality of gripper supports attached to the inflatable gripper element.

The device may further comprise at least one vacuum conduit disposed within the housing, and at least one pressure conduit disposed within the housing, wherein the vacuum conduit connects the vacuum source to the internal chamber and wherein the pressure conduit connects the pressure source to the inflatable gripper element.

The device may further comprise a movable support having a front end which adjustably supports an outside surface of the inflatable gripper element, wherein the inflatable gripper element comprises an inner wall, an outer wall, and at least one inflatable chamber disposed between the inner and outer walls which capable of being inflated, and wherein the inflatable gripper element comprises at least one of a plurality of folds which allow the inflatable gripper element to expand radially, and a plurality of gripper supports attached to the inflatable gripper element. The inflatable gripper element may comprise a textured surface which is adapted to ensure a significant amount vacuum gripping between the inflatable gripper element and the object. The at least one of the pressure source and the vacuum source may be attached to the housing. The inflatable gripper element may comprise a circular cross-sectional shape. The inflatable gripper element may comprise a polygonal cross-sectional shape. The device may further comprise a robot arm coupled to the housing. The housing may be one of axially flexible and axially bendable.

The invention also provides for a flexible vacuum gripper device comprising a housing, a gripper element defining an internal chamber and being radially expandable and comprising an inner wall, an outer wall, and at least one inflatable chamber disposed between the inner and outer walls which capable of being inflated, the inflatable gripper element having a front end which is adapted to grip an object and a rear end coupled to the housing, a vacuum source is provided for communicating with the internal chamber of the inflatable gripper element, a pressure source is also provided for communicating with the inflatable gripper, a movable support is included having a front end which adjustably supports an outside surface of the inflatable gripper element. The inflatable gripper element is adapted to be inflated using the pressure source, and the inflatable gripper element comprises at least one of a plurality of folds which allow the inflatable gripper element to expand radially, and a plurality of gripper supports attached to the inflatable gripper element.

A flexible vacuum gripper device is also provided which comprises a housing having a front end and a rear end, a movable gripper support disposed adjacent the front end of the housing, a gripper element defining an internal chamber and being radially expandable and comprising an inner wall, an outer wall, and at least one inflatable chamber disposed between the inner and outer walls which capable of being inflated, the inflatable gripper element having a front end which is adapted to grip an object and a rear end coupled to the movable gripper support, a vacuum source is provided for communicating with the internal chamber of the inflatable gripper element, and a pressure source is also provided for communicating with the inflatable gripper element. The inflatable gripper element is adapted to be inflated using the pressure source.

The invention also provides for another method of gripping an object using a flexible vacuum gripper device which includes a housing, an inflatable gripper element defining an internal chamber and being radially expandable, the inflatable gripper element having a front end adapted to grip an object and a rear end coupled to the housing, a vacuum source communicating with the internal chamber of the inflatable gripper element, and a pressure source communicating with the inflatable gripper, the method comprising positioning the inflatable gripper against the object, inflating the inflatable gripper using the pressure source, and forming a vacuum in the internal chamber using the vacuum source. The vacuum gripper device is adapted to vacuum grip the object while the inflatable gripper element is inflated.

The housing may comprise a front end and the device may further comprises a movable gripper support disposed adjacent the front end of the housing. The inflatable gripper element may comprise an inner wall, an outer wall, and at least one inflatable chamber disposed between the inner and outer walls which capable of being inflated. The rear end of the gripper element may be coupled to the movable gripper support.

The invention further contemplates a flexible vacuum gripper device comprising a housing having a front end, a gripper element defining an internal chamber and being radially expandable and comprising an inner wall, an outer wall, and at least one inflatable chamber disposed between the inner and outer walls which capable of being inflated, the inflatable gripper element having an expandable front end which is adapted to grip an object and a non-expandable rear end coupled to the movable gripper support, a vacuum source is provided for communicating with the internal chamber of the inflatable gripper element, a pressure source is also provided for communicating with the inflatable gripper element. The inflatable gripper element is adapted to be inflated using the pressure source.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
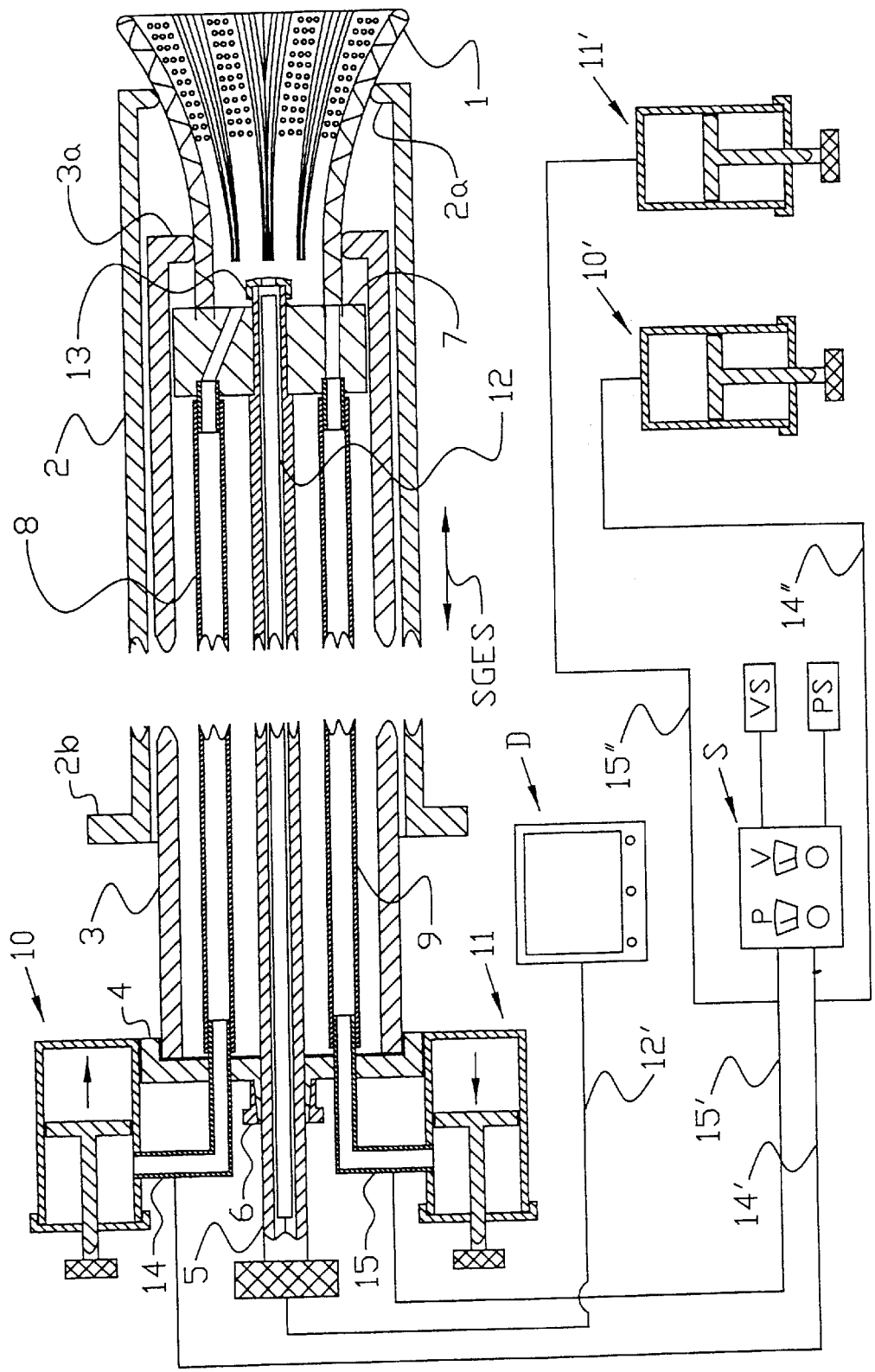
FIG. 1 shows a cross-sectional representation of one embodiment of the flexible gripper in which alternative sources of vacuum and pressure are illustrated.

FIG. 1 shows in schematic representation a flexible vacuum gripper which employs flexible gripper element 1 disposed at a front end of a housing element 3 and employing a movable and/or sliding support 2. Housing element 3 may be formed as an elongated tube whose cross-section may be of any desired shape and is preferably either of circular or polygonal in cross-section, in accordance with a corresponding cross-sectional shaped gripper element 1, as will be described more precisely herein. At a front end of housing element 3 is an in-turned rounded shoulder 3a which is adapted to provide external support to gripping element 1. This support is maintained, even when gripping element 1 is retracted and/or moved rearwardly into housing element 3 (and will cause gripper element 1 to contract radially and/or distort circumferentially inward as it is retracted into housing 3). In this regard, this design functions to control the amount of radial/circumferential expansion of gripper element 1. Such a design also serves to control the amount of gripper element 1 which is available for gripping an object, i.e., the amount of gripper element which protrudes beyond end 3a, as well as the radial and/or circumferential expansion of a front portion of gripper element 1.

Figure 6:
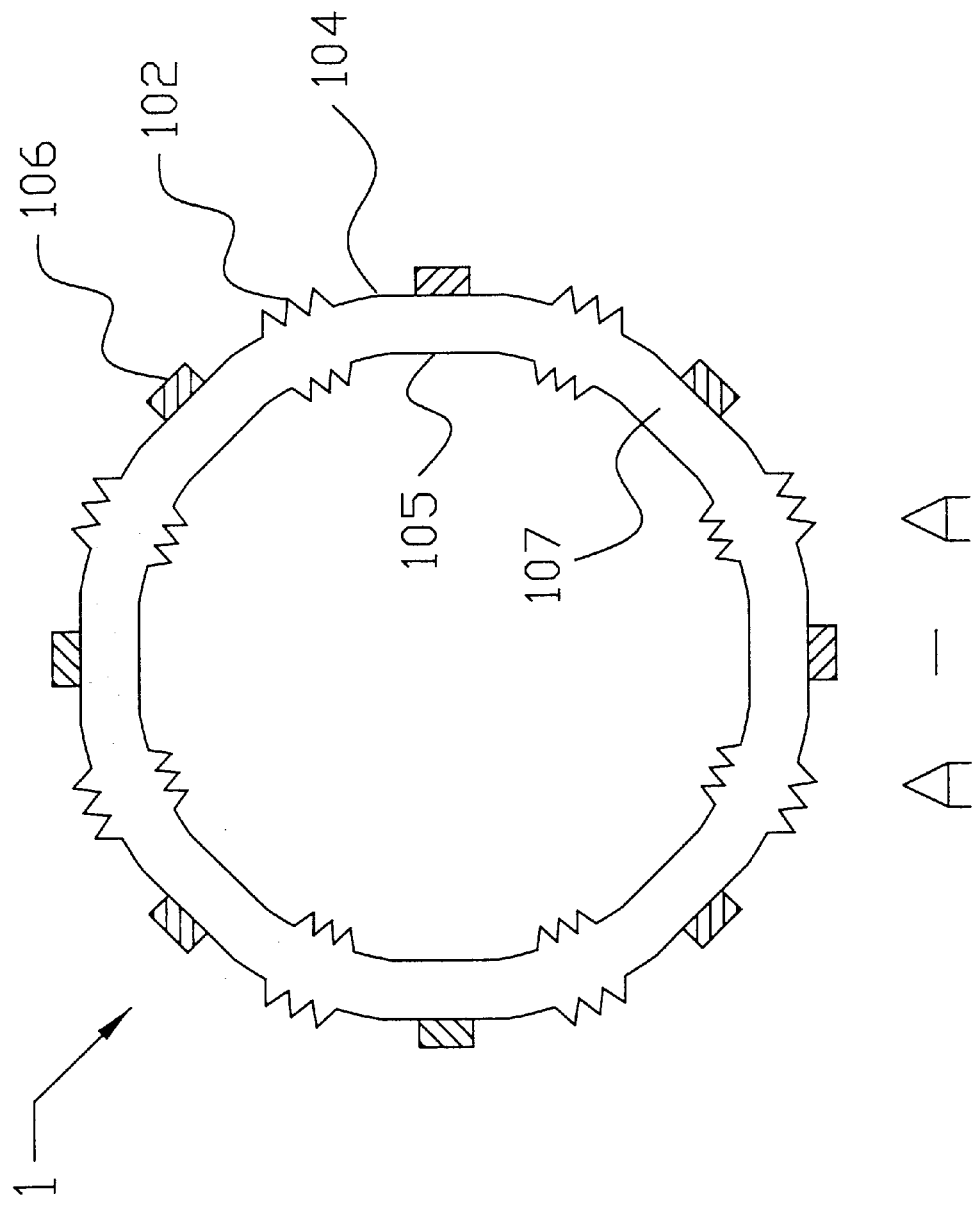
FIG. 6 shows a cross-section A—A of the gripper element of FIG. 3 in which a circular gripper element design is utilized.
Figure 7:
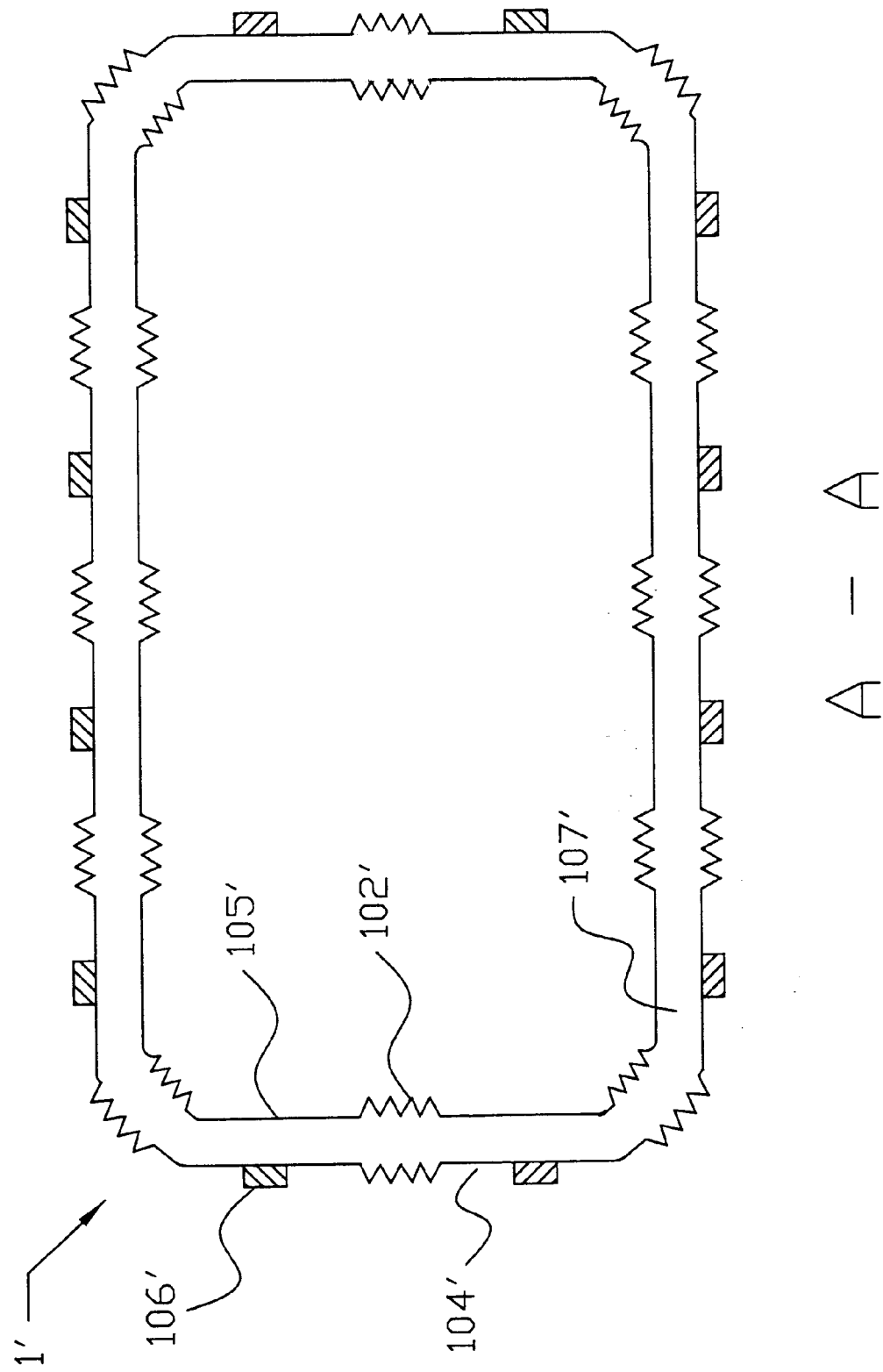
FIG. 7 shows a cross-section A—A of another possible embodiment of the gripper element of FIG. 3 in which a polygonal (e.g., 4 sided) gripper element design is utilized.

Gripper element 1 is preferably a two walled flexible structure which is designed to be inflated by a pressure medium such as air. Of course, it can also be formed as a multi-walled structure, e.g., more than two walls, to improve its rigidity and/or its resistance to failure. The advantage of this inflation is that it imparts a rigidity to the flexible structure so that when a vacuum is employed within gripper element 1, gripper element 1 is prevented from collapsing inwardly. Instead, gripper element 1 may be made of any suitable material such as rubberized canvas and is preferably made of a material which can be expanded by pressure (i.e., like a balloon), without leaking the pressure medium or bursting under the pressure. For this purpose it may be useful to make gripper element 1 from a high tensile fabric (e.g., Nylon, Nomex, or Kevlar type materials) which can be coated to prevent pressure leakage or made of a fabric which itself has a no-leak capability. It should be noted that gripper element 1 should be made of a material of sufficient thickness to operate safely when exposed to pressure. Additionally, it is also advantageous to provide a rugged sealing texture 101, 101' (see also FIG. 2) to an inside front portion of gripper element 1 in order to facilitate good sealing to the object, as well as good/reliable gripping of an irregular surface of the object to be gripped. Such a surface may include a raised silicone or rubber surface and/or it may be formed as a plurality of raised sealing bumps which act to increase the friction between the object and gripper element 1. Gripper element 1 is also preferably formed with folds 102, 102' (see also FIGS. 6 and 7) which allow gripper element 1 to expand and contract radially/circumferentially to accommodate objects of varying size. Folds 102, 102' may have an accordion shape and may act to assist in contracting gripper element 1 (i.e., having a memory like a spring) when the pressure is reduced within walls 104 and 105. Inner wall 105 portion of folds 102, 102' of gripper element 1 may also have similar texturing 101 (not shown).

It should also be noted that the invention contemplates a gripper element 1 which operates using any type of pressure medium such as gas or fluid/hydraulic pressure. However, air or inert gas under pressure is preferred. In the case of fluid mediums, the material of gripper element 1 may have to be made stronger in order to withstand greater pressures associated with hydraulic systems.

Figure 2:
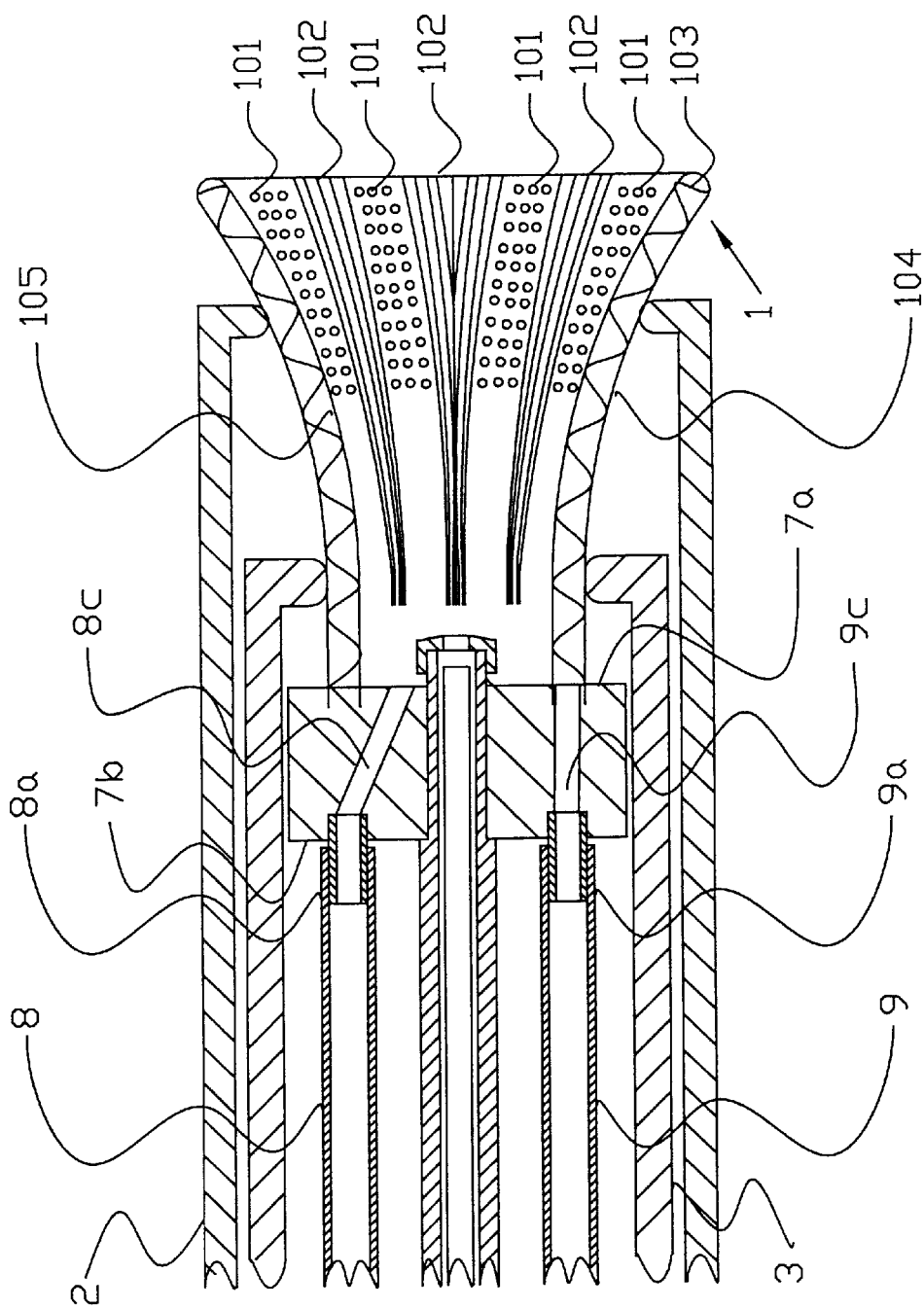
FIG. 2 shows a front portion of the flexible gripper depicted in FIG. 1.

As can be seen in FIG. 2, gripper element 1 is formed as a two walled inflatable structure in which inner wall 105 has a rear end which is connected to gripper support 7 and an outer wall 104 having a rear end connected to gripper support 7. The particular connection between rear ends of walls 104 and 105 to gripper support 7 is not shown in detail. However, it is clear that this connection must be made secure and leak-tight. In this regard, any type of connection may be utilized such as and adhesive, bonding, welding, and/or a mechanical type connection (provided it results in a reliable pressure seal).

In one advantageous embodiment, gripper support 7 is made of a plastic and gripper element 1 has ends which are formed with plastic attaching ends, e.g., rings, (not shown) such that the attaching ends are ultrasonically welded to gripper support 7.

A connecting/spacing system is provided to maintain walls 104 and 105 in a predetermined arrangement. In this regard, a plurality of connecting stitches 103 may be employed to connect inner wall 105 and outer wall 104 in order to form the two walled structure forming gripper element 1. Connecting stitches 103 may be made of any suitable material, but should preferably be made of high tensile threads and/or wires in order to resist failure when gripper element experiences pressure inflation. In this embodiment, front end portions of walls 104 and 105 are integrally connected so as to form a rounded end, i.e., in this example of the invention inner wall 105 and outer wall 104 are made from a single piece of material which is folded to form the rounded end. However, it should be noted that gripper element 1 may be formed in any manner which advantageously produces an inflatable structure capable of being pressurized from within.

Referring back to FIG. 1, it can be seen that gripper support 7 is movable within housing element 3 by virtue of it being connected to gripper extender rod 5 via a threaded connection. Of course, any connection may be utilized here. Moreover, gripper extender rod 5 constitutes a hollow rod, made of a convenient light weight material such as composite, resin, plastic, or aluminum, having a front end which is capped with a transparent window device or lens cap 13, whose advantage will be herein described. At rear end of extender rod 5 is disposed a knob 5b which allows a user to manipulate and/or move gripper support 7/gripper element 1 forwardly and rearwardly within housing element 3. Of course, in an automated or robotic application, rear end of rod 5 would be connected to a controllable actuator type device (not shown). A locking mechanism 6 may also be utilized to lock extender rod 5 from moving axially with respect to housing element 3. In this regard, locking mechanism 6 may be a collet type locking mechanism which uses oppositely arranged tapered threads to apply a compressive force against gripper extender rod 5. Additionally, extender rod 5 is preferably formed as hollow so as to be adapted to allow a viewing device 12, such as an optical fiber type camera device, to be inserted within its hollow space. In this regard, the advantage of lens cap 13 is realized to allow viewing of the object which is being gripped by gripper element 1. It goes without saying that lens cap 13 should be sealing connected to extender rod 5 in order to prevent the loss of vacuum pressure, when an object is gripped by gripper element 1.

One or more pressure carrying conduits 9 are utilized to provide pressure to inflate/pressurize gripper element 1. These conduits 9 are preferably flexible in an axial direction in order to allow gripper support 7 to move forwardly. In this regard, conduits 9 may also be of sufficient length so as to be conveniently folded within housing element 3 (not shown). Alternatively, specialized conduits 9, e.g., having an axially flexible accordion design/shape, may be utilized (not shown) in order to allow for axial movement of gripper support 7 without subjecting conduits 9 to axial stretching/tensile forces.

The advantage of using more than one conduit 9 is that gripper element 1 can be pressurized/inflated by zones. In this regard, gripper element 1 may be constructed with a number of inflatable zones, in which each zone is pressurized by a respective conduit 9 (not shown). The advantage of this design is that one or more zones can loose pressure and/or fail without compromising the reliability/function of the entire gripper element 1. An alternative advantage is that the pressure of each zone can be varied to provide better sealing of gripper element 1 on an object.

Referring back to FIG. 1, it is clear that this design allows for a pressure medium such as air pressure to be delivered to inflatable gripper element 1. This is facilitated via one or more connecting openings 9c formed in gripper support 7. These openings allowing an end 9a of conduit 9 to deliver the pressure medium to inflate/pressurize gripper element 1. Of course, there should be as many openings 9c as there are conduits 9 and pressure zones in gripper element 1.

One or more vacuum carrying conduits 8 are also utilized to provide negative pressure within gripper element 1. As with pressure conduits 9 above, conduits 8 are preferably flexible in an axial direction in order to allow gripper support 7 to move forwardly. In this regard, a sufficient length of conduits 8 may be folded within housing element 3 (not shown). Alternatively, specialized conduits 8, e.g., having an axial accordion shape, may be utilized (not shown) in order to allow for axial movement of gripper support 7. It is clear that this design allows for the creation of a negative pressure medium, i.e., a vacuum, to be formed within inflatable gripper element 1. This is facilitated via one or more connecting openings 8c formed in gripper support 7. These openings 8c allowing an end 8a of conduit 8 to extract air from within gripper element 1. Although not shown, it may be advantageous to provide a filtering mechanism, e.g., a screen, within gripper element 1 in order to prevent dirt and other particles from clogging openings 8c.

Figure 3:
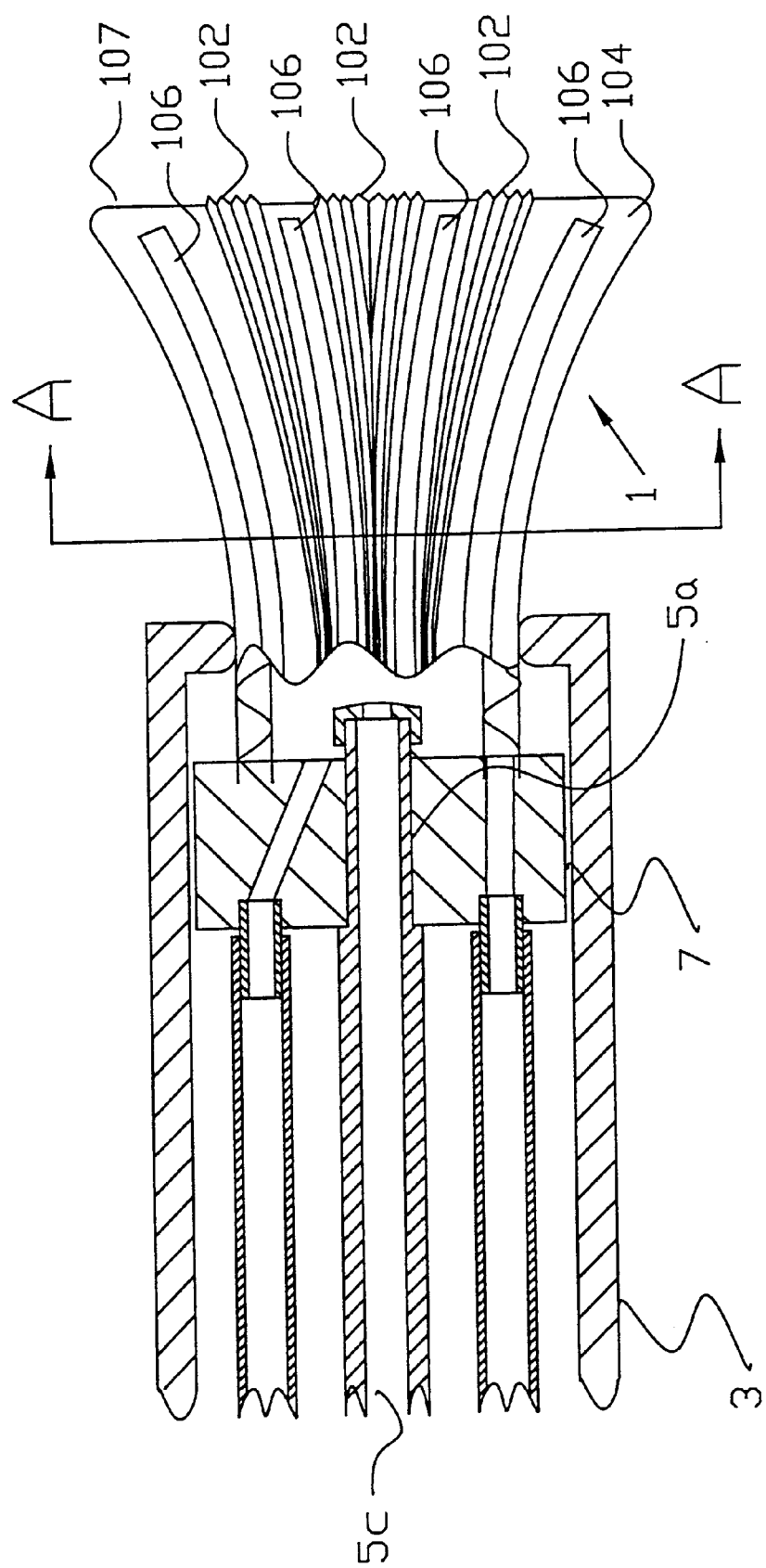
FIG. 3 shows another cross-sectional representation of the flexible gripper depicted in FIG. 1 with the exterior of the gripper element being shown.

Referring now to FIG. 3, it can be seen that gripper element 1 may also advantageously utilize support elements 106 arranged between folds 102 and 102', e.g., accordion type folds, on outer wall 105 of gripper element 1. Of course, support elements 106 may also be walls 104 and 105, and even on inside wall 105, 105' as long as they don't adversely affect the ability of gripper element 1 to grip an object. Support elements 106 function to externally support gripper element 1 as is shown. However, support elements 106 also function as springs in that they act to force gripper element 1 to contract radially/circumferentially inwards when the pressure is reduced within the walls 104, 105 of gripper element 1. In this regard, supports 106 may be formed of any material which functions in this manner and are preferably formed of spring steel. They may be made of any desired material and they may also have any desired shape, e.g., wire shaped, bar shaped, tube shaped, or elongated rectangular shaped members, as shown. Moreover, they may be attached to gripper element 1, and specifically, outer wall 105 by any conventional attachment mechanism such a adhesive bonding.

Figure 4:
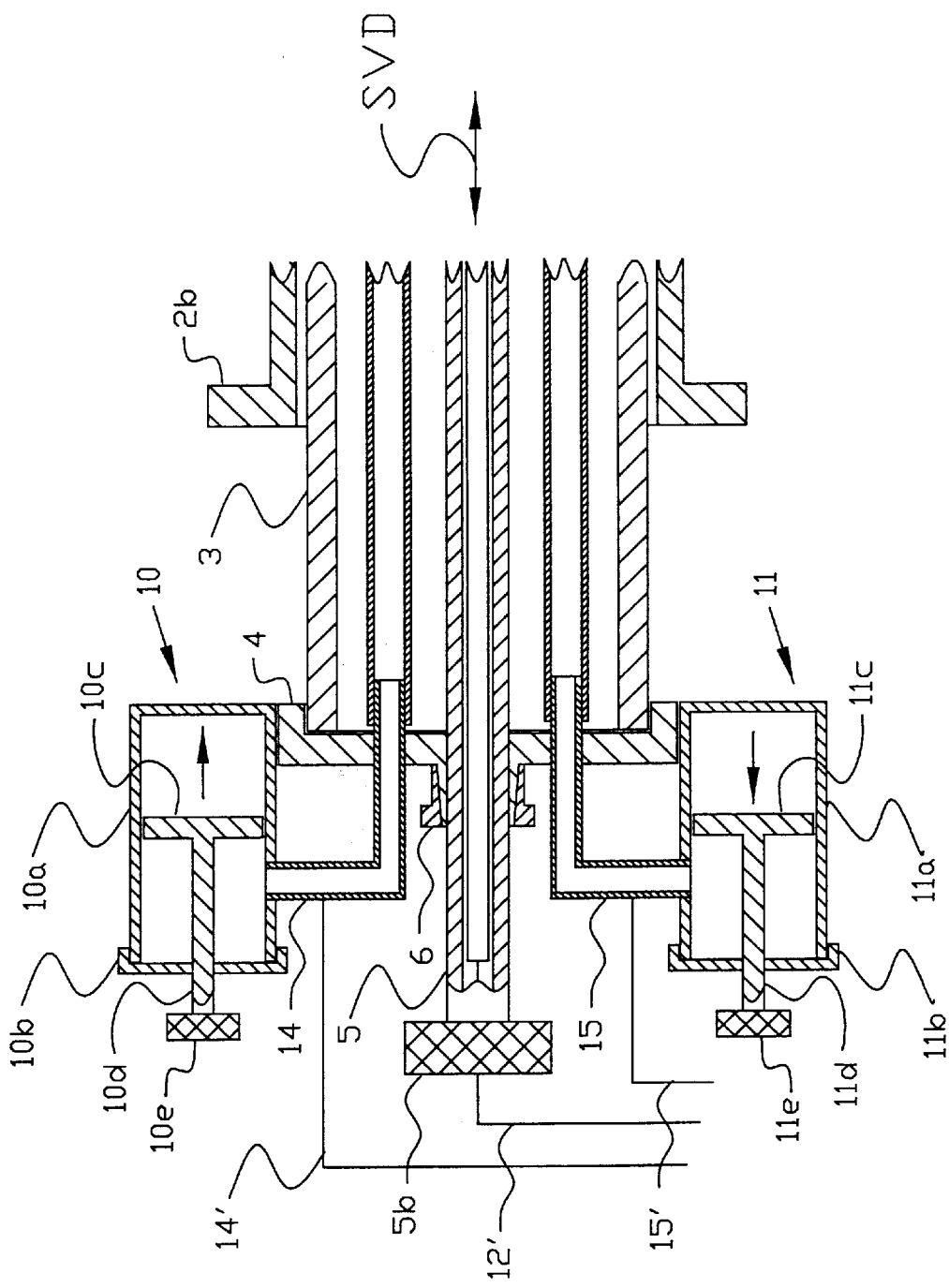
FIG. 4 shows a rear portion of the flexible gripper depicted in FIG. 1.

As the details of the vacuum and pressure sources are generally known, so the invention will describe these only briefly. Referring to FIG. 4, a rear end of the flexible vacuum gripper is shown using an attached vacuum 10 and pressure 11 sources. Vacuum source 10 is constructed a cylinder 10a and piston 10c design in which a piston rod 10d is moved via a push mechanism 10e. Cylinder 10a forms a chamber which is closed by a cap 10b. A connecting port 14 is provided for communicating with vacuum supply conduit 8 to produce a vacuum within gripper element 1. It is clear that movement of piston 10e in the direction of arrow (see FIG. 1) will cause a vacuum to be created inside port 14.

Similarly, pressure source 11 is constructed as a cylinder 11a and piston 11c design in which a piston rod 11d is moved via a push mechanism 11e. Cylinder 11a is also formed as a chamber which is closed by a cap 11b. A connecting port 15 communicates with pressure supply conduit 9 to produce pressure inside walls 104 and 105 of gripper element 1. It is clear that movement of piston 11e in the direction of arrow (see FIG. 1) will cause a pressure to be created inside port 15.

Figure 5:
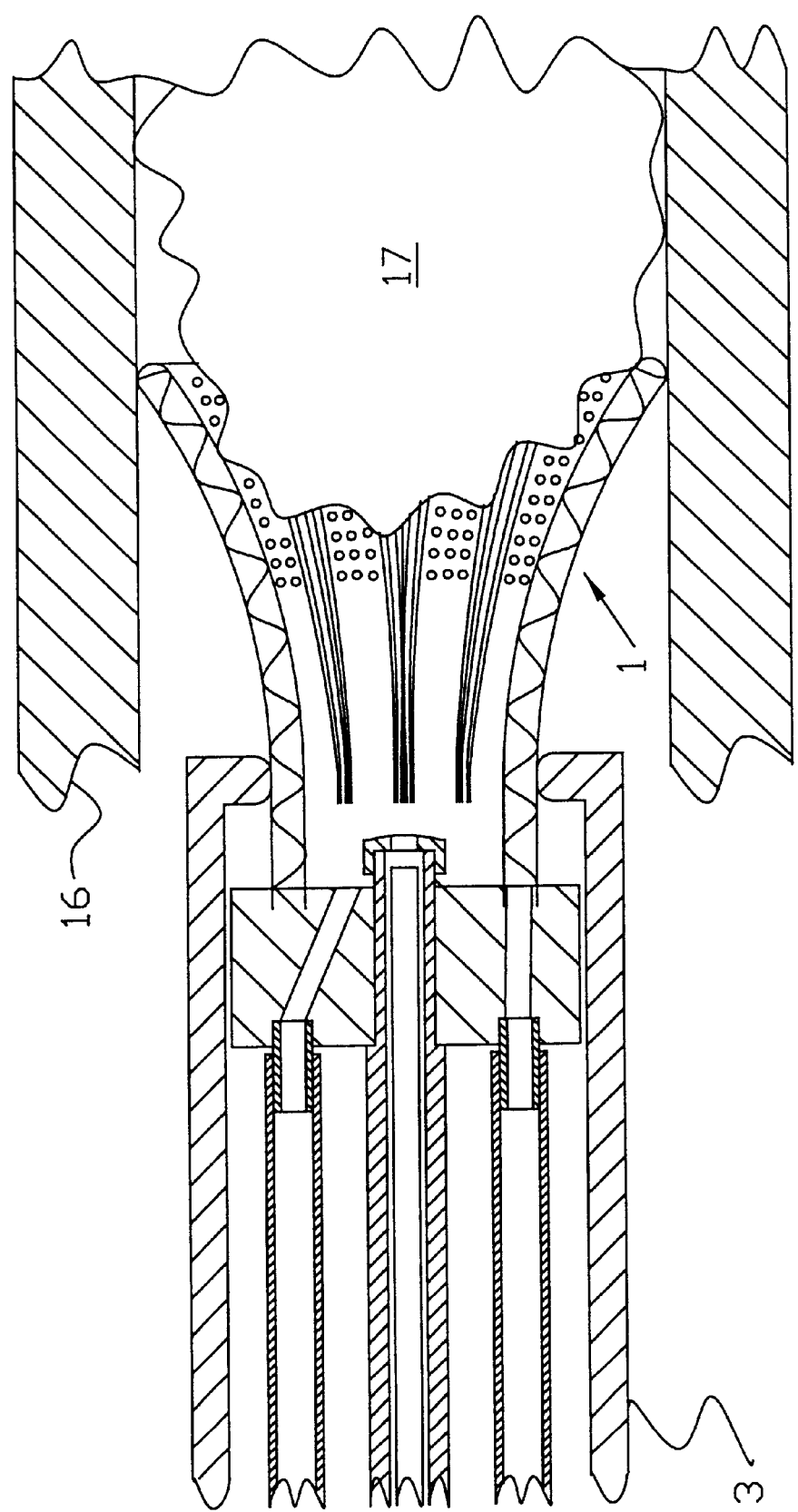
FIG. 5 shows a possible use of the an even more simplified version of the embodiment of the flexible gripper depicted in FIG. 1.

FIG. 5, illustrates one possible use of the invention. In this case, a simplified version of the invention is utilized to grip an object 17 which is lodged within a passage or tunnel 16. It is clear that because the object 17 is trapped with its sides engaging the walls of tunnel 16, that gripper element 1 cannot grip the object 17 from the sides. Accordingly, the invention has particular advantage in this case when only a front part of the object 17 is available for gripping. The fact that the front part of the object 17 may have an irregular surface is no obstacle to the invention because gripper element 1 can conform to irregular shapes.

The invention also has the ability of controlling the amount of the gripper element 1 which extends past housing element 3a, by movement of gripper support 7. Moreover, by varying the pressure within the walls 104, 105 of gripper element 1, its rigidity can be adapted and/or controlled to the specific irregularity of the object's surface. Such adaptation allows gripper element 1 to conform to the irregular shape in order to provide for a good vacuum seal between surface 104 (and especially surface 101) and the irregular surface of the object. Of course, the invention would also function very well with symmetrical and smooth surfaced objects.

Figure 8:
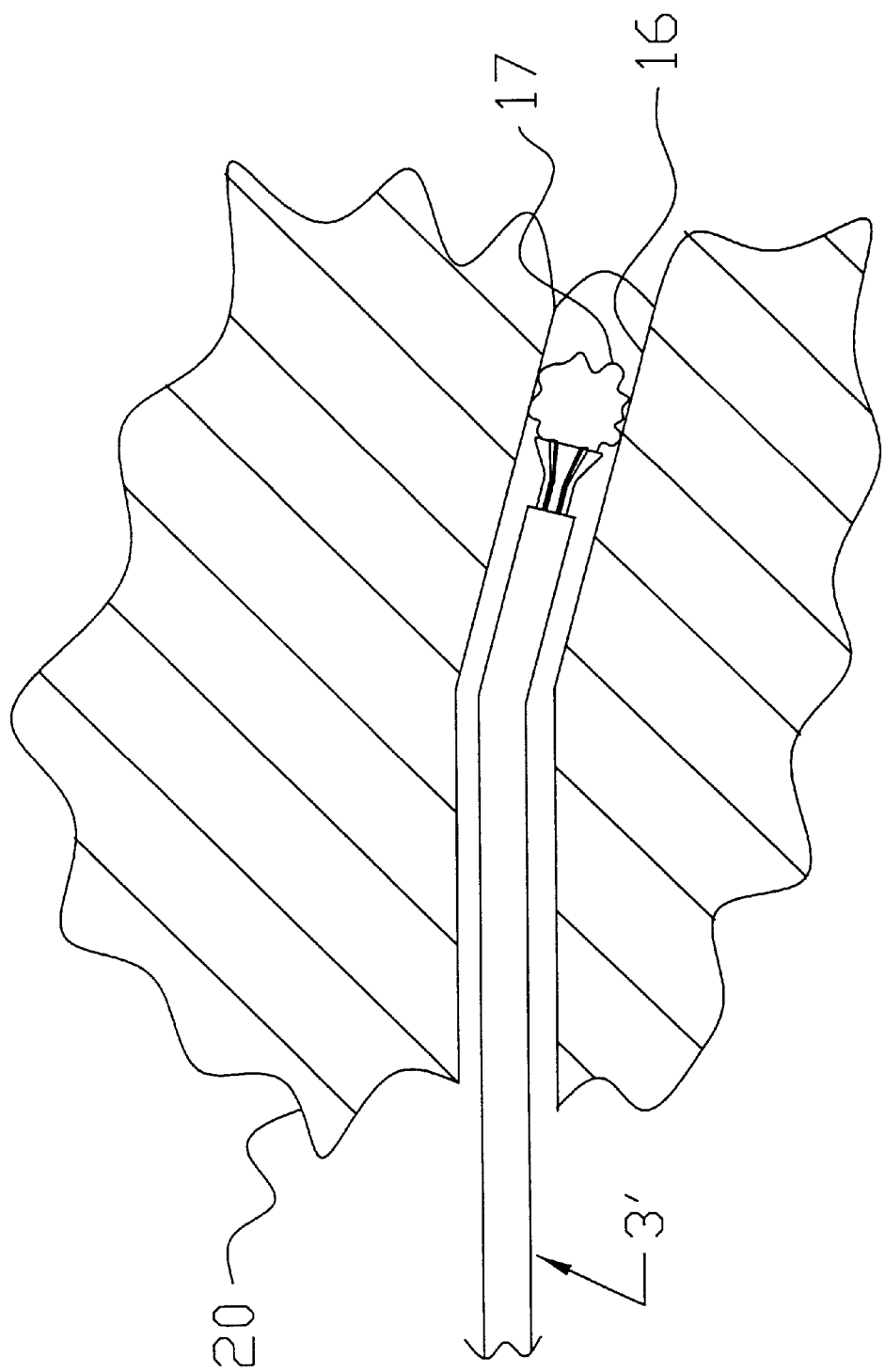
FIG. 8 shows another possible use of the an even more simplified version of the embodiment of the flexible gripper depicted in FIG. 1 in which a bendable and/or axially flexible elongated housing element is utilized to reach down to objects which are trapped within a non-straight tunnel, the objects being located a significant distance from a tunnel entrance.

FIG. 8, illustrates another possible use of the invention. In this case, a simplified version of the invention is utilized to grip an object 17 which is lodged deep within a passage or tunnel 16 which may not be straight. Again, it is clear that because the object 17 is trapped with its sides engaging the walls of tunnel 16, that gripper element 1 cannot grip the object 17 from its sides. Accordingly, the invention has particular advantage when only a front part of the object 17 is available for gripping. The fact that the front part of the object 17 may have an irregular surface is no obstacle to the invention. In this regard, the invention uses a flexible housing element 3' design which can be bend in conformance with passage 16. Accordingly, housing element 3' can be formed as a bendable tube like structure. It may also be formed with an axial accordion shape or in the manner of the outer sheath of, e.g., a speed-odometer cable. Again, the invention has the ability of controlling the amount of the gripper element 1 which extends past housing element 3a by movement of gripper support 7. As in the above embodiment, by varying the pressure within the walls 104, 105 of gripper element 1, its rigidity can be adapted to the specific irregularity of the object's surface. Such adaptation allows gripper element 1 to conform to the irregular shape of the object, in order to provide for a good vacuum seal between surface 104 (and especially surface 101) and the irregular surface of the object. Again, the invention would also function very well with symmetrical and/or smooth surfaced objects such as spheres or plates.

Figure 9:
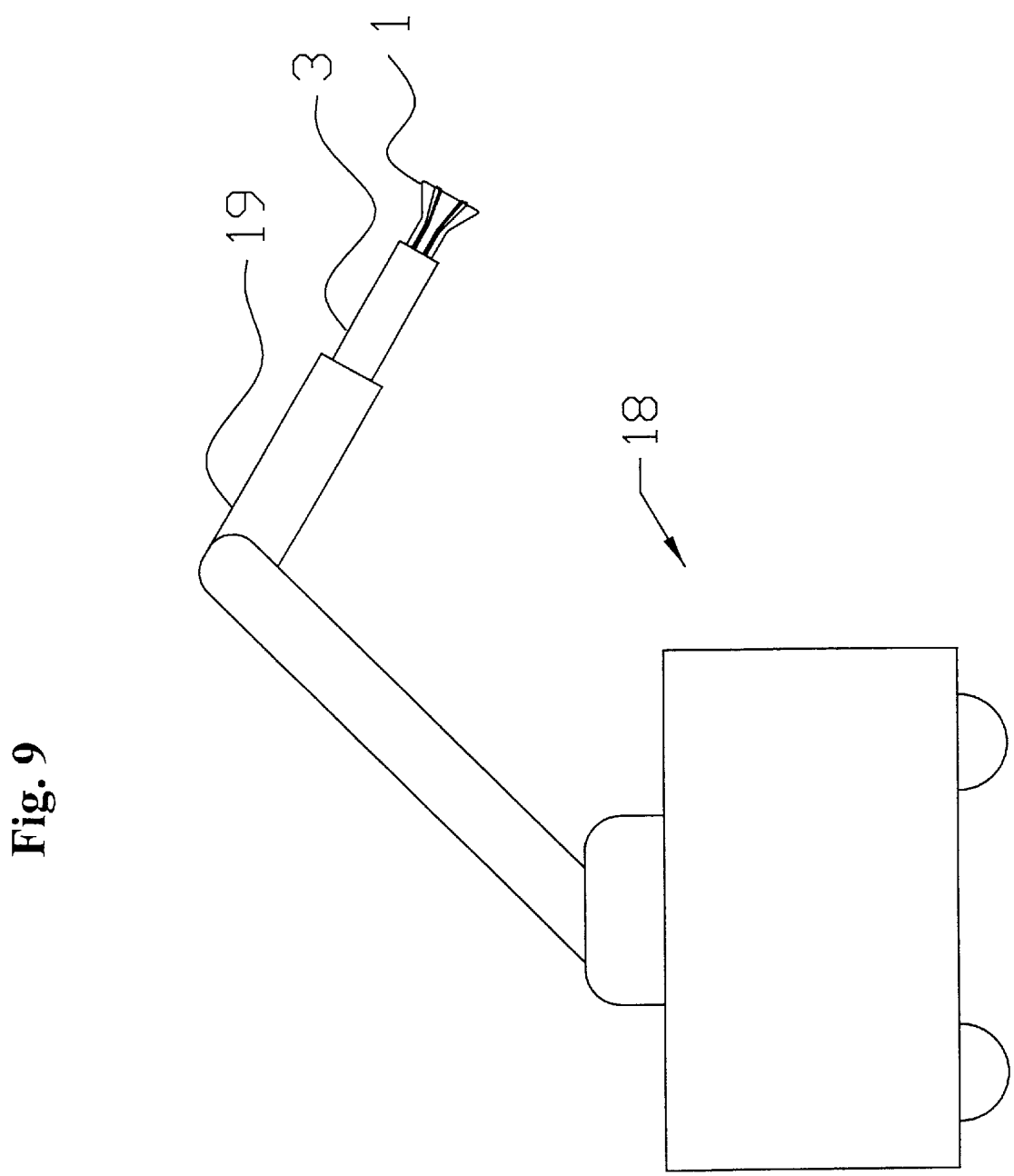
FIG. 9 shows a possible use of a simplified version of the embodiment of the flexible gripper depicted in FIG. 1, in which the flexible gripper is used on a robotic device, such as a mobile robot, the flexible gripper being installed at the end of a robot arm.

FIG. 9, illustrates another possible use of the invention. In this case, a simplified version of the invention is utilized to grip objects which are not trapped within a tunnel. Instead, the flexible vacuum gripper is utilized at the end of a robot arm 19. The arm 19 may further be attached to a mobile robot 18. Accordingly, the invention may have particular advantage when gripping irregularly shaped objects such as land mines. Again, the invention has the ability of controlling the amount of the gripper element 1 which extends past housing element 3a by movement of gripper support 7, in this case using robotic control. As in the above embodiment, by varying the pressure within the walls 104, 105 of gripper element 1, its rigidity can be adapted to the specific irregularity of the object's surface. Such adaptation allows gripper element 1 to conform to the irregular shape in order to provide for a good vacuum seal between surface 104 (and especially surface 101) and the irregular surface of the object. The invention would also function very well with symmetrical and smooth surfaced objects.

The flexible gripping device may also utilize a number of additional design options. A sliding support 2, in the form of tubular structure, may be employed to add additional external support to inflatable gripper element 1. The advantage of this optional feature is that gripper element 1 is kept from expanding beyond a desired range relative to the object being gripped. By utilizing a combination of external support via sliding support 2 and varying the pressure in gripper element 1, a user can precisely control the expansion of gripper element 1 up to a desired point for gripping. In this regard, sliding support 2 may have a front end with a rounded in-turned part 2a which is adapted to engagingly support, i.e., prevent excessive expansion of, gripper element 1. An opposite end 2b is adapted to be moved by a user to control the amount of sliding of support 2. Of course, in an automated or robotic application, rear end of support 2 would be connected to a controllable actuator type device (not shown). As is evidenced from this design, each of housing element 3 and sliding support 2 are cylindrical and/or tubular in shape to correspond to a circular shape of gripper element 1 (see, e.g., FIG. 6). However, it should be noted the cross-sectional shape of housing element 3 and sliding support 2 may be of any desired shape such a polygonal to correspond to a particular shape of gripper element (see, e.g., FIG. 7). Of course, other shapes are also contemplated. It should be noted that sliding support 2 and housing element 3 may be formed of any convenient light weight material, e.g., composite, plastic, resin, aluminum, titanium, ect.

One design option uses attached vacuum 10 and pressure 11 sources. These are respectfully connected to a rear end of the flexible gripping assembly via connecting conduits 14 and 15 respectively, as is shown in FIG. 1. However, an alternative embodiment provides that the vacuum 10' and pressure 11' sources are separated (i.e., not attached) from the gripping device, in which connecting conduits 14' and 15' are utilized to allow the gripping device to be made easier to use. Another embodiment provides for an electronic control S of the negative and positive pressures rendering the device even more easy to use. Such a device S would employ pressure adjustment knobs and gages to allow the user to precisely control both the vacuum generated within gripper element 1, as well as the inflation pressure inside gripper element 1. Such a device may also have the form of a control device S which utilizes a separate connected vacuum source VS and pressure source PS.

Still another design option uses a monitor or display D in combination with viewing device 12, as is shown in FIG. 1. This design allows the user to see the gripping operation from within gripper element 1. In this regard, a user can see whether the object is being gripped effectively and/or what effect changing the pressure and vacuum has on gripper element 1, i.e., how well gripper element 1 grips the object. It is clear that such a design would utilize a magnifying type lens cap 13 to facilitate detailed viewing.

Figure 10:
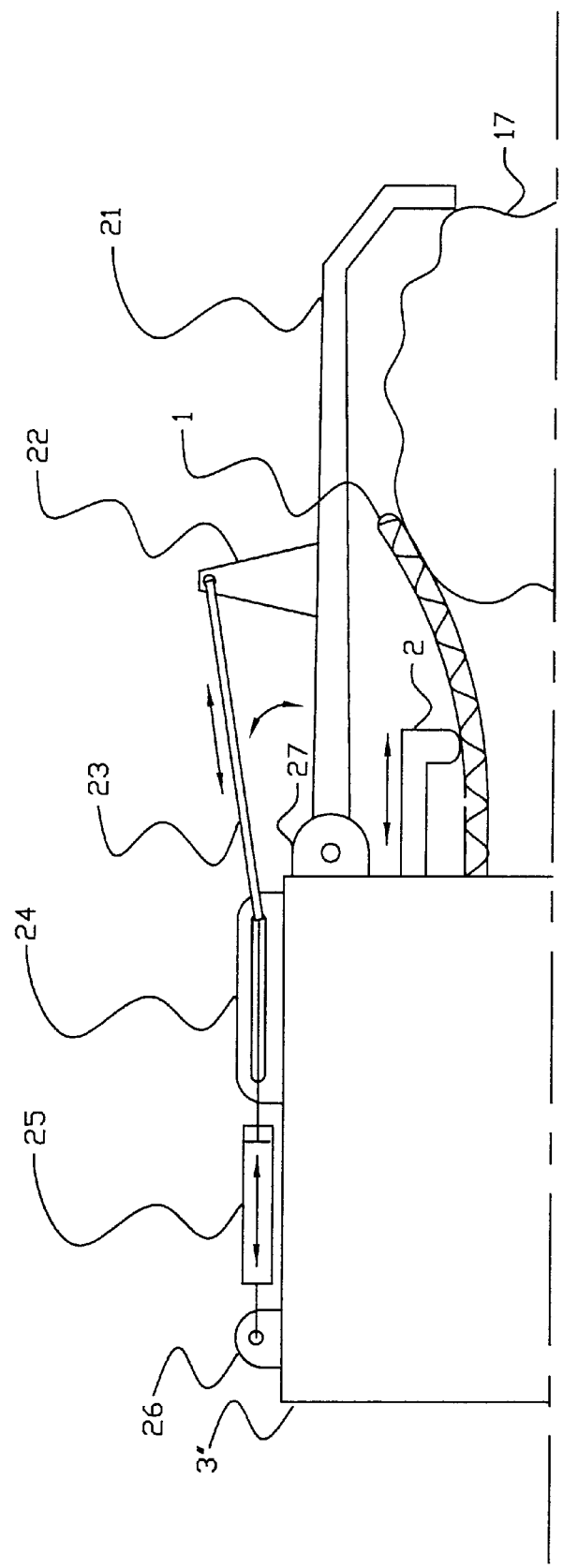
FIG. 10 shows another embodiment of a flexible gripper which utilizes many of the features depicted in FIG. 1 and which includes an additional securing mechanism for ensuring that the object is doubly and mechanically secured.

FIG. 10 shows another embodiment of the invention (only half the device is shown because the other half would be identical, i.e., mirror image) in which the operation of gripper element 1, sliding support 2 and housing element 3" function similarly to the embodiment shown in FIG. 1. However, in this embodiment a mechanical object retaining system is included to further mechanically secure/retain the object. The advantage of this embodiment is that either the vacuum or pressure, or both, may be turned off after its initial use to grip the object. Thereafter, the object is mechanically secured. Such as design may also be used to enhance the gripping of the flexible gripper element 1 by providing a mechanism which "backs-up" the vacuum gripping with mechanical gripping. In this regard, this embodiment similarly uses vacuum and pressure (not shown) to operate the gripper element 1 but further included the mechanical object retaining system.

The system includes oppositely arranged pivot retaining arms 21 which are pivotally connected to housing 3". Arms 21 have a connecting bracket 22 which is connected to a strut 23. A guide mechanism 24 is attached to housing 3". Guide mechanism has a channel which confines a rear end portion of strut 23 between a minimum and a maximum movement position. An actuator 25 which may be a piston/cylinder unit is employed to move rear end of strut 23 within guide mechanism and between the minimum and maximum positions. Actuator 25 has a rear end connected to housing 3" via a bracket 26. It is clear to one having ordinary skill in the art how such a system functions. Nevertheless, its function can be briefly described as follows: Upon actuation of actuator (e.g., a controlled electric signal in the case of an electromechanical actuator and a controlled pressure signal in the case of a pneumatic or hydraulic actuator), strut 23 is caused to move to the position shown, i.e., a maximum position. Of course, operating the actuator in reverse, will pivot arm 21 away from object until a rear portion of strut reaches a minimum position in guide mechanism (not shown). Such possible movements are indicated by the various arrows. It should be noted that the invention contemplates two, four, six, ect. oppositely arranged arms and devices 22–26. Moreover, such an embodiment may have particular application as a hand for a robot type device with the mechanical retaining system being coupled/controlled by the robot system in the same way as the sliding support 2, and vacuum and gripper element pressure are controlled.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE CHARACTERS

1 Flexible gripper element
2 Sliding support
3 Housing element
4 Housing cover
5 Gripper extender rod
6 Locking member
7 Gripper support
8 Vacuum supply conduit
9 Pressure supply conduit
10 Vacuum source
11 Pressure source
12 Viewing device
13 lens cap
14 Vacuum connection
15 Pressure connection
16 Tunnel
17 Object
18 Mobile Robot
19 Robot arm
20 Tunnel entrance
21 Arm
22 Bracket
23 Strut
24 Guide mechanism
25 actuator
26 Bracket
101 Textured surface
102 Flexible folds
103 Connecting stitches
104 Outer wall
105 Inner wall
106 Gripper supports
SGES Sliding gripper element support movement
SVD Sliding viewing device movement
S Modular vacuum/pressure source
VS Separate vacuum source
PS Separate pressure source
D Display
P Pressure
V Vacuum

What is claimed:

1. A flexible vacuum gripper device comprising:

a housing;

an inflatable gripper element defining an internal chamber and comprising a rear portion coupled to the housing and a front portion which can be one of radially and circumferentially expandable;

the front end being conformable to the shape of an object and being expandable by inflation when not gripping the object;

a vacuum source communicating with the internal chamber of the inflatable gripper element;

a pressure source communicating with the inflatable gripper element; and at least one of;

a movable gripper support being fixed to the rear end portion of the gripper element for allowing the gripper element to move axially with respect to the housing, and the front end portion of the gripper element comprising a plurality of folds which are arranged substantially parallel to an axis through the housing and the inflatable gripper element, wherein the vacuum gripper device is adapted to grip the object using vacuum formed in the internal chamber and wherein the inflatable gripper element is adapted to be inflated using the pressure source".

2. The device of claim 1, wherein the rear portion of the inflatable gripper element is non-expandably coupled to the movable gripper support.

3. The device of claim 1, wherein the housing comprises a front end which engagingly supports an outside surface of the inflatable gripper element.

4. The device of claim 1, further comprising a movable support which engagingly supports an outside surface of the inflatable gripper element.

5. The device of claim 1, wherein the inflatable gripper element comprises an inner wall, an outer wall, and at least one inflatable chamber disposed between the inner and outer walls.

6. The device of claim 1, further comprising a viewing device adapted to view the internal chamber of the inflatable gripper element.

7. The device of claim 1, wherein the movable gripper support is coupled to movable extender rod disposed within the housing.

8. The device of claim 7, wherein the movable extender rod comprises a tube which adapted to receive a viewing device and wherein the device further comprises a lens cap disposed at a front end of the extender rod.

9. The device of claim 1, further comprising:
a movable support having a front end which adjustably supports an outside surface of the inflatable gripper element, and
the inflatable gripper element comprising an inner wall, an outer wall, and at least one inflatable chamber disposed between the inner and outer walls.

10. The device of claim 1, wherein the plurality of folds allow the inflatable gripper element to expand radially, and further comprising a plurality of gripper supports attached to the inflatable gripper element.

11. The device of claim 1, further comprising:
at least one vacuum conduit disposed within the housing; and
at least one pressure conduit disposed within the housing, wherein the vacuum conduit connects the vacuum source to the internal chamber and wherein the pressure conduit connects the pressure source to the inflatable gripper element.

12. The device of claim 1, further comprising:
a movable support having a front end which adjustably supports an outside surface of the inflatable gripper element,
the inflatable gripper element comprising an inner wall, an outer wall, and at least one inflatable chamber disposed between the inner and outer walls which capable of being inflated, and
the inflatable gripper element comprising a plurality of gripper supports attached to the inflatable gripper element.

13. The device of claim 1, wherein at least the front portion of inflatable gripper element comprises a textured surface which is adapted to ensure a significant amount vacuum gripping between the inflatable gripper element and the object.

14. The device of claim 1, wherein at least one of the pressure source and the vacuum source is attached to the housing.

15. The device of claim 1, wherein the inflatable gripper element comprises one of a circular cross-sectional shape and a polygonal cross-sectional shape.

16. The device of claim 1, further comprising a robot arm coupled to the housing.

17. The device of claim 1, wherein the housing is one of axially flexible and axially bendable.

18. The device of claim 1, further comprising a mechanism for additionally retaining the object, the mechanism comprising at least two substantially oppositely arranged arms which are movable towards and away from the object.

19. A flexible vacuum gripper device comprising:
a housing having a front end;
a gripper element defining an internal chamber and being radially or circumferentially expandable;
the gripper element comprising an inner wall, an outer wall, a plurality of stitches connecting the inner wall and the outer wall, and at least one inflatable chamber disposed between the inner and outer walls which capable of being inflated;
the inflatable gripper element having an expandable and conformable front end which is adapted to grip an object and a rear end coupled to the front end of the housing;
a vacuum source communicating with the internal chamber of the inflatable gripper element;
a pressure source communicating with the inflatable gripper element; and
one of;
a movable gripper support being fixed to the rear end of the gripper element for allowing the gripper element to move axially with respect to the housing, or
the front end of the gripper element comprising a plurality of folds which are arranged substantially parallel to an axis through the housing,
wherein the inflatable gripper element is adapted to be inflated using the pressure source.

20. A method of gripping an object using a flexible vacuum gripper device which includes a housing, an inflatable gripper element defining an internal chamber and being radially expandable, the inflatable gripper element having a front end adapted to grip an object and a rear end coupled to the housing, a vacuum source communicating with the internal chamber of the inflatable gripper element, and a pressure source communicating with the inflatable gripper element, the method comprising:
adjusting a position of the inflatable gripper element with respect to the housing by moving the inflatable gripper element towards or away from the housing;
positioning the inflatable gripper element against the object;
inflating the inflatable gripper element using the pressure source; and
forming a vacuum in the internal chamber using the vacuum source,
wherein the vacuum gripper device is adapted to vacuum grip the object while the inflatable gripper element is inflated, and
wherein the inflatable gripper element is radially expandable by inflation when not gripping the object.

* * * * *